(12) United States Patent
Lowe et al.

(10) Patent No.: US 8,828,970 B2
(45) Date of Patent: Sep. 9, 2014

(54) METHODS OF MAKING AND USING A RUMINANT GAS REDUCTION COMPOSITION

(75) Inventors: Matthew W. Lowe, Lufkin, TX (US); Anne Chace Hopkins, Diboll, TX (US); Thomas A. Lehtinen, Diboll, TX (US)

(73) Assignee: Georgia-Pacific Wood Products LLC, Atlanta, GA (US)

( * ) Notice: Subject to any disclaimer, the term of this patent is extended or adjusted under 35 U.S.C. 154(b) by 0 days.

(21) Appl. No.: 13/392,288

(22) PCT Filed: Aug. 26, 2010

(86) PCT No.: PCT/US2010/046867
§ 371 (c)(1),
(2), (4) Date: Feb. 24, 2012

(87) PCT Pub. No.: WO2011/031531
PCT Pub. Date: Mar. 17, 2011

(65) Prior Publication Data
US 2012/0225841 A1 Sep. 6, 2012

Related U.S. Application Data

(60) Provisional application No. 61/237,396, filed on Aug. 27, 2009.

(51) Int. Cl.
A23K 1/18 (2006.01)
A23K 1/16 (2006.01)

(52) U.S. Cl.
CPC .............. *A23K 1/1643* (2013.01); *A23K 1/1813* (2013.01)
USPC ......................................... 514/54; 536/123.1

(58) Field of Classification Search
CPC ........................... A23K 1/1813; A23K 1/1643
USPC ......................................... 514/54; 536/123.1
See application file for complete search history.

(56) References Cited

U.S. PATENT DOCUMENTS

| | | |
|---|---|---|
| 2,453,142 A | 11/1948 | Lee |
| 3,733,405 A | 5/1973 | Derrig |
| 3,796,797 A | 3/1974 | Parish et al. |
| 3,878,298 A | 4/1975 | Parish et al. |
| 3,988,483 A | 10/1976 | Deyoe et al. |
| 4,820,527 A | 4/1989 | Christensen et al. |
| 5,756,098 A | 5/1998 | Price et al. |
| 6,241,983 B1 | 6/2001 | Paul et al. |
| 6,783,780 B1 | 8/2004 | De Jong et al. |
| 7,048,937 B2 | 5/2006 | Dawson et al. |
| 7,109,005 B2 | 9/2006 | Eroma et al. |
| 7,291,607 B2 | 11/2007 | Day et al. |
| 7,625,728 B2 | 12/2009 | Eroma et al. |
| 7,638,151 B2 | 12/2009 | Duan et al. |
| 7,772,212 B2 | 8/2010 | Day et al. |
| 7,842,490 B2 | 11/2010 | Felby et al. |
| 7,993,689 B2 | 8/2011 | Duan et al. |
| 8,137,706 B2 | 3/2012 | Al-Ghazzewi et al. |
| 2003/0162300 A1 | 8/2003 | Kunz et al. |
| 2004/0091537 A1 | 5/2004 | Miller |
| 2004/0175460 A1 | 9/2004 | Zenovich |
| 2004/0176320 A1 | 9/2004 | Natunen et al. |
| 2005/0064447 A1 | 3/2005 | Huang |
| 2005/0079244 A1 | 4/2005 | Giffard et al. |
| 2005/0288250 A1 | 12/2005 | Rautonen et al. |
| 2006/0034978 A1 | 2/2006 | Deem et al. |
| 2006/0051812 A1 | 3/2006 | Helin et al. |
| 2006/0068022 A1 | 3/2006 | Playford |
| 2006/0182708 A1 | 8/2006 | Bockmuhl et al. |
| 2007/0141678 A1 | 6/2007 | Green et al. |
| 2007/0196890 A1 | 8/2007 | Vulevic et al. |
| 2007/0243268 A1 | 10/2007 | Jaffe |
| 2007/0298014 A1 | 12/2007 | Huang |
| 2009/0004327 A1 | 1/2009 | Duan et al. |
| 2009/0304852 A1 | 12/2009 | Hopkins et al. |
| 2010/0028485 A1 | 2/2010 | Tuohy et al. |
| 2013/0018015 A1 | 1/2013 | Hopkins et al. |

FOREIGN PATENT DOCUMENTS

| | | |
|---|---|---|
| EP | 0143490 A2 | 6/1985 |
| EP | 1407037 B1 | 4/2004 |
| EP | 2025242 A1 | 2/2009 |
| GB | 2404561 A | 2/2005 |

(Continued)

OTHER PUBLICATIONS

De Castro FB. The use of steam treatment to upgrade lignocellulosic materials for animal feed. Ph. D. Thesis, University of Aberdeen. Sep. 1994.*

(Continued)

*Primary Examiner* — Brandon Fetterolf
*Assistant Examiner* — Yih-Horng Shiao
(74) *Attorney, Agent, or Firm* — Michael V. Kruljac; Ram W. Sabnis

(57) ABSTRACT

A method comprising administering an oligosaccharide composition to an organism having a gastrointestinal system to affect the production of GHG produced by the organism allowing for a reduction of the GHG produced by the organism while optimizing the health, feed intake, and protein synthesis of the organism so that management of the organism may realize the synergistic effects of maximizing both typical organism commodity-type concerns (e.g., size and production metrics) and atypical organism commodity-type concerns (e.g., carbon credit trading/monetization). A gas-reducing composition comprising soluble extractable material from a lignocellulosic source. A method of producing a composition, comprising providing a lignocellulosic source; extracting soluble materials from the lignocellulosic source to produce soluble extractable material; and processing the soluble extractable material to yield a gas-reducing composition, wherein the gas-reducing composition comprises hemicellulose and exhibits gas-reducing activity.

18 Claims, 6 Drawing Sheets

(56) References Cited

FOREIGN PATENT DOCUMENTS

| JP | 2004229607 A | 8/2004 |
|---|---|---|
| JP | 2005027541 A | 2/2005 |
| JP | 4078778 B2 | 4/2008 |
| KR | 1019910004110 A | 3/1991 |
| KR | 100597659 B1 | 6/2006 |
| WO | 0033854 A1 | 6/2000 |
| WO | 03015533 A1 | 2/2003 |
| WO | 2004000340 A2 | 12/2003 |
| WO | 2005111195 A2 | 11/2005 |
| WO | 2005111195 A3 | 11/2005 |
| WO | 2007091231 A1 | 8/2007 |
| WO | 2009117790 A2 | 10/2009 |
| WO | 2009152089 A2 | 12/2009 |
| WO | 2009152089 A3 | 12/2009 |
| WO | 2010089453 A1 | 8/2010 |
| WO | 2011031531 A2 | 3/2011 |
| WO | 2011031531 A3 | 3/2011 |
| WO | 2011072051 A2 | 6/2011 |

OTHER PUBLICATIONS

Allision, Milton J., et al., "*Synergistes jonesii*, gen. nov., sp. nov.: A rumen bacterium that degrades toxic pyridinediols," System. Appl. Microbiol., 1992, pp. 522-529, vol. 15, Gustax Fischer Verlag, Stuttgart/ New York.

Azumi, H., et al., "Xylo-oligosaccharide composition is useful as medicine with high regulation effect of intestinal condition and is not decomposed by digestive fluids," XP-002656403 and JP 2001-226409 A, WPI Thomson, abstract, Aug. 21, 2001, 10 pages.

Bar-Shavit, Zvi, et al., "Mannose-binding activity of *Escherichia coli*: A determinant of attachment and ingestion of the bacteria by macrophages," Aug. 1980, pp. 417-424, vol. 29, No. 2, Infection and Immunity.

Chaney, Albert L., et al., "Modified reagents for determination of urea and ammonia," 1962, pp. 130-132, vol. 8, No. 2, Clinical Chemistry.

Crawford, D. F., et al., "Evaluation of concentrated hemicellulose extract as cattle feed," XP-002580031, Journal of Animal Science, 1978, vol. 46, No. 1, pp. 32-40.

Ebringerová, Anna, et al., "Norway spruce galactoglucomannans exhibiting immunomodulating and radical-scavenging activities," International Journal of Biological Macromolecules, 2008, pp. 1-5, vol. 42, Elsevier B.V.

Foreign communication from a related counterpart application—International Search Report and Written Opinion, PCT/US2009/046605, Jan. 20, 2010, 7 pages.

Foreign communication from a related counterpart application—International Search Report and Written Opinion, PCT/US2010/046867, Jun. 1, 2011, 11 pages.

Foreign communication from a related counterpart application—Supplementary European Search Report, Application No. EP 09763380.4, Aug. 23, 2011, 11 pages.

Foreign communication from a related counterpart application—International Search Report and Written Opinion, PCT/US2010/059528, Aug. 30, 2011, 10 pages.

Foreign communication from a related counterpart application—International Preliminary Report on Patentability, PCT/US2010/046867, Feb. 28, 2012, 7 pages.

Gedek, B. R., "Adherence of *Escherichia coli* serogroup 0 157 and the *Salmonella typhimurium* mutant DT 104 to the surface of *Saccharomyces boulardii*," Mycoses, 1999, pp. 261-264 plus 1 page publishing information, vol. 42, © 2002 EBSCO Publishing.

González-Muñoz, M. J., et al., "Production of hemicellulosic sugars from *Pinus pinaster* wood by sequential steps of aqueous extraction and acid hydrolysis," Wood Sci Technol, 2012, pp. 271-285, vol. 46, Springer-Verlag.

Jouany, Jean-Pierre, "Rumen microbial metabolism and ruminant digestion," 1991, pp. 217-237 plus 2 pages cover and publishing information, INRA Editions, Paris.

Mandre Malle, et al., "The quality of stemwood of *Pinus sylvestris* in an alkalised environment," Water Air Soil Pollut, 2007, pp. 163-172, vol. 182, Springer Science + Business Media B.V.

Mirelman, David, et al., "Screening of bacterial isolates for mannose-specific lectin activity by agglutination of yeasts," Apr. 1980, pp. 328-331, vol. 11, No. 4, Journal of Clinical Microbiology.

Moure, Andrés, et al., "Advances in the manufacture, purification and applications of xylo-oligosaccharides as food additives and nutraceuticals," XP-002656401, Process Biochemistry, 2006, vol. 41, pp. 1913-1923, Elsevier Ltd.

Nabarlatz, Debora Alcida, "Autohydrolysis of agricultural by-products for the production of xylo-oligosaccharides," Dissertation, Departament d'Enginyeria Química, Universitat Rovira I Virgili, Sep. 29, 2006, pp. 1-4, 19-22, and cover page, Tarragona.

Nacos, M. K., et al., "*Kenaf xylan*—a source of biologically active acidic oligosaccharides," Carbohydrate Polymers, 2006, vol. 66, issue 1, pp. 126-134, Elsevier Ltd.

Advisory Action dated Feb. 2, 2012 (3 pages), U.S. Appl. No. 12/480,171, filed Jun. 8, 2009.

Office Action dated Apr. 7, 2011 (18 pages), U.S. Appl. No. 12/480,171, filed Jun. 8, 2009.

Office Action (Final) dated Oct. 3, 2011 (11 pages), U.S. Appl. No. 12/480,171, filed Jun. 8, 2009.

Office Action dated Apr. 25, 2012 (12 pages), U.S. Appl. No. 12/480,171, filed Jun. 8, 2009.

Parajó, J.C., et al., "Production of xylooligo-saccharides by autohydrolysis of lignocellulosic materials," Trends in Food Science & Technology, 2004, vol. 15, pp. 115-120, Elsevier Ltd.

Pietarinen, Suvi, P., et al., "Knotwlle and bark extracts: strong antioxidants from waste materials," J Wood Sci, 2006, pp. 436-444, vol. 52, The Japan Wood Research Society.

Provisional patent application entitled "Natural prebiotic derived from southern yellow pine polysaccharides," by Tom Lehtinen, et al., filed Dec. 9, 2008 as U.S. Appl. No. 61/121,005.

Provisional patent application entitled "Oligosaccharide prebiotic product processed from softwood molasses," by Tom Lehtinen, et al., filed Jun. 9, 2008 as U.S. Appl. No. 61/059,960.

Provisional patent application entitled "Ruminant gas reduction composition and methods of making and using the same," by Matthew W. Lowe, et al., filed Aug. 27, 2009 as U.S. Appl. No. 61/237,396.

Provisional patent application entitled "Nutritional composition and methods of making and using same," by Anne Chase Hopkins, et al., filed Dec. 8, 2009 as U.S. Appl. No. 61/267,570.

Salanitro, J. P., et al., "Quantitative method for the gas chromatographic analysis of short-chain monocarboxylic and dicarboxylic acids in fermentation media," Applied Microbiology, Mar. 1975, pp. 374-381, vol. 29, No. 3, American Society for Microbiology.

Vázquez, M.J., et al., "Enhancing the potential of oligosaccharides from corncob autohydrolysis as prebiotic food ingredients," Industrial Crops and Products, 2006, vol. 24, pp. 152-159, Elsevier, Ltd.

Vázquez, M.J., et al., "Enzymatic processing of crude xylo-oligomer solutions obtained by autohydrolysis of Eucalyptus wood," XP002656402, Food Biotechnology, abstract, 2002, 1 page.

Vázquez, M.J., et al., "Refining of autohydrolysis liquors for manufacturing xylo-oligosaccharides: evaluation of operational strategies," XP 025313229, Bioresource Technology, 2005, vol. 96, pp. 889-896, Elsevier, Ltd.

Vázquez, M. J., et al., "Xylooligosaccharides: manufacture and applications," Trends in Food Science & Technology, 2000, pp. 387-393, vol. 11, Elsevier Science Ltd.

Willför, Stefan, et al., "Spruce-derived mannans—A potential raw material for hydrocolloids and novel advanced natural materials," XP-002656400, Carbohydrate Polymers, 2008, pp. 197-210, vol. 72, Elsevier Ltd.

Foreign Communication from a related counterpart application—International Preliminary Report on Patentability, PCT/US2010/059528, Jun. 21, 2012, 8 pages.

Patent application entitled "Nutritional Composition and Methods of Making and Using Same," by Anne Chace Hopkins, et al., filed Jun. 8, 2012 as U.S. Appl. No. 13/514,885.

Foreign Communication from a related counterpart application—European Examination Report, European Patent Application No. 09763380A, May 23, 2012, 3 pages.

\* cited by examiner

Effect of GROC on total gas production during *in vitro* incubation of ruminal contents supplemented with 0.02 g ground alfalfa and GROC as indicated. Means with unlike letter designations differ ($P < 0.05$).

Effect of GROC on hydrogen production during *in vitro* incubation of ruminal contents supplemented with 0.02 g ground alfalfa and GROC as indicated. Means with unlike letter designations differ ($P < 0.05$).

Effect of GROC on methane production during *in vitro* incubation of ruminal contents supplemented with 0.02 g ground alfalfa and GROC as indicated. Means with unlike letter designations differ ($P < 0.05$).

Effect of GROC on carbon dioxide production during *in vitro* incubation of ruminal contents supplemented with 0.02 g ground alfalfa and GROC as indicated. Means with unlike letter designations differ ($P < 0.05$).

Effect of GROC on final pH during *in vitro* incubation of ruminal contents supplemented with 0.02 g ground alfalfa and GROC as indicated. Means with unlike letter designations differ ($P < 0.05$).

Effect of GROC on ammonia accumulation during *in vitro* incubation of ruminal contents supplemented with 0.02 g ground alfalfa and GROC as indicated. Means with unlike letter designations differ ($P < 0.05$).

METHODS OF MAKING AND USING A RUMINANT GAS REDUCTION COMPOSITION

CROSS-REFERENCE TO RELATED APPLICATIONS

This application is a filing under 35 U.S.C. 371 of International Application No. PCT/US2010/046867 filed Aug. 26, 2010, entitled "Methods of Making and Using a Ruminant Gas Reduction Composition," claiming priority of U.S. Provisional Patent Application No. 61/237,396 filed Aug. 27, 2009, which applications are incorporated by reference herein in their entirety.

BACKGROUND

Greenhouse gases ("GHG") are gases in an atmosphere that absorb and emit radiation within the thermal infrared range. The primary greenhouse gases in the Earth's atmosphere are water vapor, carbon dioxide, methane, nitrous oxide, and ozone.

The 2010 United States federal budget proposes to support clean energy development with a 10-year investment of $15 billion per year, generated from the sale of GHG emissions credits. Under the proposed cap-and-trade program, all GHG emissions credits would be auctioned off, generating an estimated $78.7 billion in additional revenue in FY 2012, steadily increasing to $83 billion by FY 2019.

Emissions trading is a market-based approach used to control pollution by providing economic incentives for achieving reductions in the emissions of pollutants. Governing entities may establish a limit or cap on the amount of a pollutant that can be emitted. Such limit or cap may be applied, allocated, or sold to entities which have been identified as capable of producing emissions at a level which could be subject to the established limit or cap for said designated pollutants. These limits or caps may be applied, allocated, or sold to such emissions entities in the form of emissions permits which represent the right to emit or discharge a specific volume of a specified pollutant. Such emission producing entities are required to hold a number of permits (or credits) equivalent to their emissions. The total amount of permits (or credits) issued by the governing entity cannot exceed the cap; thus, limiting total emissions to that level. Emissions entities that need to increase their level of emissions must buy permits from those who require fewer permits. The transfer of permits is referred to as a trade. In effect, the buyer is paying a charge for polluting, while the seller is being rewarded for having reduced emissions.

The overall goal of an emissions trading plan is to minimize the cost of meeting a set emissions target. The cap is an enforceable limit on emissions that is usually lowered over time—aiming towards a national emissions reduction target. In other systems a portion of all traded credits must be retired, causing a net reduction in emissions each time a trade occurs. Thus, in theory, by limiting or capping polluting emissions the totality of pollution may be decreased. Moreover, those who can reduce emissions most cheaply will do so, achieving pollution reduction at the lowest cost to society.

There are active trading programs in several air pollutants. For GHG the largest is the European Union Emission Trading Scheme. In the United States there is a national market to reduce acid rain and several regional markets in nitrogen oxides. In 2003, New York State proposed and attained commitments from nine Northeast states to form a cap-and-trade carbon dioxide emissions program for power generators, called the Regional Greenhouse Gas Initiative. This program launched on Jan. 1, 2009 with the aim to reduce the carbon "budget" of each state's electricity generation sector to 10% below their 2009 allowances by 2018. Also in 2003, U.S. corporations were able to trade $CO_2$ emission allowances on the Chicago Climate Exchange under a voluntary scheme. In August 2007, the Exchange announced a mechanism to create emission offsets for projects within the United States that cleanly destroy ozone-depleting substances.

Since February 2007, seven U.S. states and four Canadian provinces have joined together to create the Western Climate Initiative, a regional GHG emissions trading system. July 2010, a meeting took place to further outlined the cap-and-trade system which if accepted would curb GHG emissions by January 2012.

In 2006, the California Legislature passed the California Global Warming Solutions Act, AB-32. Project based offsets have been suggested for five main project types. A carbon project would create offsets by showing that it has reduced carbon dioxide and equivalent gases. The project types include: building energy, landfill gas capture, forestry, and manure management.

According to Food and Agriculture Organization statistics, ruminant livestock-derived methane has been estimated at 18% of the total global GHG emissions on a carbon dioxide equivalency basis. In addition, global protein consumption more than doubled since 1970 and is projected to double again by 2050. Ruminant-derived methane is produced during digestion (fermentation) of feed and fodder through microbial fermentation within the rumen. Ruminant methane levels are attributable to the rate, efficiency, and completeness of carbohydrate and protein conversion from feedstuffs into volatile fatty acids ("VFAs"). The molar percentage and composition of ruminal VFAs produced during fermentation influence the production of methane. Acetate and butyrate promote methane production while propionate formation is considered a competitive pathway for hydrogen use in the rumen.

There is an inverse relationship between fermentation efficiency and methane production within the rumen. Metabolic energy loss during rumen digestion can be attributed to heat loss during fermentation, as well as the production of ammonia and methane gas. Methane reduction within the rumen not only improves GHG emissions but is attributable to increased energy conversion and subsequent enhanced animal productivity. These benefits are of key interest to farmers and producers.

Feed (diet) and feeding strategies have demonstrated significant influence on fermentation products and energy production within ruminant animals. Rumen bypass protein products are an exceptional example of how nutritional manipulation can benefit animal productivity. Methane reducing feed additives, many of which are plant-based, however, have shown limited holistic success, or have demonstrated adverse trade-offs that have precluded their widespread practical application. These negative effects include reduced feed intake and protein synthesis, both of which can limit optimal growth and development. Natural feed additives which could improve dry matter digestion and reduce methane production would represent an appealing solution for reducing livestock-derived GHG while contributing to optimal animal nutrition. Thus, the natural feed additives described herein may allow farmers and producers to maximize their food commodity production, benefit from emissions trading programs, comply with greenhouse gas emission mandates, regulations, and contribute to a better global environment.

SUMMARY

Disclosed herein is an oligosaccharide composition comprising soluble extractable material from a lignocellulosic source wherein the soluble extractable material comprises a hemicellulose. In an embodiment, the soluble extractable material comprises galactoglucomannans, xylans, arabinoxylans, or combinations thereof. In another embodiment the soluble extractable material comprises galactoglucomannans and the galactoglucomannans comprise glucose monosaccharide units, galactose monosaccharide units, and mannose monosaccharide units in a ratio of about 3 to about 1 to about 6. In an embodiment, the lignocellulosic source comprises the above and below-ground portion of a plant wherein the above-ground portion of a plant exhibits cambial growth. In another embodiment, the lignocellulosic source comprises a member of the family Pinaceae, a member of the family Fagaceae, a member of the order Saxifragales, a member of the order Pinales, or combinations thereof. In yet another embodiment, the lignocellulosic source comprises a member of the genus *Pinus*. In another embodiment an admixture comprises the oligosaccharide composition and one or more pharmaceutical carriers.

Also disclosed herein is a method comprising administering the oligosaccharide composition to an organism to reduce the production of rumen-produced methane gas.

Also disclosed herein is a method comprising administering the oligosaccharide composition to an organism to reduce the production of ruminal ammonia.

Also disclosed herein is a feed product comprising the oligosaccharide composition.

Also disclosed herein is an admixture of the oligosaccharide composition with one or more feed products, feed liquids, feed supplements, or combinations thereof.

Also disclosed herein is a method of producing a composition, comprising a lignocellulosic source; extracting soluble materials from the lignocellulosic source to produce soluble extractable material; and processing the soluble extractable material to yield a gas reducing composition, wherein the composition comprises hemicellulose and exhibits the ability to reduce methane and ammonia production in ruminants. In an embodiment extracting soluble materials comprises softening the lignocellulosic source. In an embodiment softening of the lignocellulosic source comprises autohydrolysis, pulping, steam explosion, steam extrusion, or combinations thereof. In an embodiment the hemicellulose comprises monomers, oligosaccharides, and polysaccharides having a degree of polymerization from 1 to greater than about 500. In an embodiment the hemicellulose comprises xylans, arabinoxylans, galactoglucomannans, manans, derivatives thereof, or combinations thereof. In an embodiment the soluble extractable materials comprise monosaccharides, oligosaccharides, and polysaccharides composed of glucose, galactose, and mannose units in a ratio of about 3 to about 1 to about 6. In an embodiment, the method further comprises hydrolyzing the soluble extractable materials to produce a hydrolyzed composition. In an embodiment, the hydrolyzed composition comprises polysaccharides having a degree of polymerization of from about 2 to about 20. In an embodiment, the method further comprises dehydrating the soluble extractable materials.

Also disclosed herein is a method comprising administering the oligosaccharide composition to an organism having a gastrointestinal system. In an embodiment administration of the oligosaccharide composition reduces the production of methane and/or ammonia within the organism.

Also disclosed herein is a method comprising administering the oligosaccharide composition to an organism having a gastrointestinal system. In an embodiment administration of the oligosaccharide composition reduces the production of ruminal methane and/or ammonia within the organism.

Also disclosed herein is a method of managing livestock comprising supplementing the livestock's diet with a gas reducing composition comprising soluble extractable material from a lignocellulosic source, quantifying, or having quantified, a reduction in gas produced by the livestock subsequent to the supplementation and realizing an economic or other benefit from the reduction in gas produced.

Also disclosed herein is a method of managing livestock comprising determining a baseline amount of greenhouse gases produced by the livestock, administering to the livestock a gas reducing composition comprising soluble extractable material from a lignocellulosic source, determining an amount of greenhouse gases produced by the livestock subsequent to administering the gas reducing composition, calculating a reduction in greenhouse gases by subtracting the amount of greenhouse gases produced by the livestock subsequent to administering the gas reducing composition to the baseline amount of greenhouse gases produced by the livestock, and receiving an economic benefit from the reduction in greenhouse gases produced by the livestock.

Also disclosed herein are a method and system comprising administering the oligosaccharide composition to an organism having a gastrointestinal system to affect the production of GHG produced by the organism allowing for a reduction of the GHG produced by the organism to be quantified and utilized in an emissions trading program, for compliance with emission-related mandates, or to meet the requirements of emission regulations.

Also disclosed herein are a method and system comprising administering the oligosaccharide composition to an organism having a gastrointestinal system to affect the production of GHG produced by the organism allowing for a reduction of the GHG produced by the organism while optimizing the health, feed intake, and protein synthesis of the organism so that management of the organism may realize the synergistic effects of maximizing both typical organism commodity-type concerns (e.g., size and production metrics) and atypical organism commodity-type concerns (e.g., carbon credit trading/monetization).

DETAILED DESCRIPTION

Figure 1:
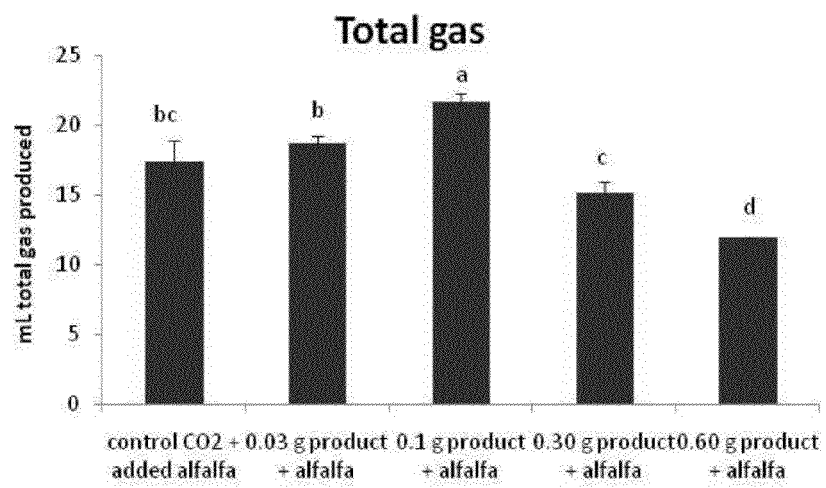
FIG. 1 represents the effect of the gas reducing oligosaccharide composition ("GROC") on total gas production during in vitro incubation of ruminal contents supplemented with 0.02 g ground alfalfa.
Figure 2:
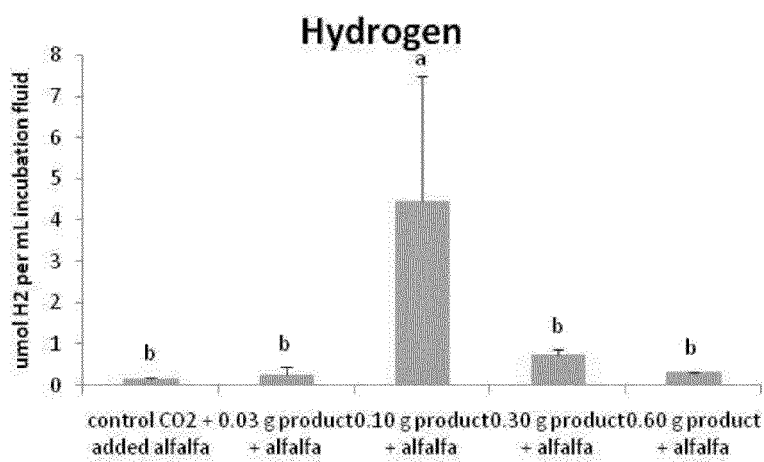
FIG. 2 represents the effect of GROC on hydrogen production during in vitro incubation of ruminal contents supplemented with 0.02 g ground alfalfa.

Although an illustrative implementation of one or more embodiments may be provided below, the disclosed systems and/or methods may be implemented using any number of techniques. This disclosure should in no way be limited to the illustrative implementations, drawings, and techniques illustrated below, including the exemplary designs and implementations illustrated and described herein, but may be modified within the scope of the appended claims along with their full scope of equivalents.

Disclosed herein is a gas reducing oligosaccharide composition ("GROC") and methods of making and using same. In an embodiment, the gas comprises any gas produced by and subsequently expelled from an organism of the type to be described in more detail later herein. Alternatively, the gas comprises methane, ammonia, or combinations thereof. In an embodiment, the GROC comprises soluble extractable materials from a lignocellulosic source. In an embodiment, the GROC is derived from a renewable, biological source material such as wood, bark, foliage, and roots. As is understood by those of skill in the art, wood refers to the organic material produced as secondary xylem in the stems of trees comprising various biological polymers including cellulose, hemicellulose, pectin, and lignin.

In an embodiment, the GROC is derived from a lignocellulosic source material. Herein the term "derived" refers to isolation of the material from an organism where it is present natively such that the material is no longer in contact with all components of its native milieu. In an embodiment, the GROC is derived from the above-ground or below-ground portion of a plant source material. In another embodiment the GROC is derived from a lignocellulosic source material that exhibits cambial growth. For example, the source material may comprise a plant that is a member of the order Pinales, the family Pinaceae, the family Fagaceae or the order Saxifragales. Alternatively the source material is derived from a member of the family Pinaceae. The family Pinaceae comprises coniferous trees commonly known as the pine family.

In embodiments, the source material comprises a material derived from a member of the genus *Pinus*. The genus *Pinus* comprises coniferous trees commonly known as the pines. In embodiments, the source material comprises a material derived from a member of at least one species collectively referred to as the Southern Yellow Pines. In embodiments, the source material comprises a material derived from a member of the species *Pinus taeda* L, and its hybrids commonly referred to as Loblolly Pine. In alternative embodiments, the source material comprises a material derived from a member of the species *Pinus elliotii* Englem, and its hybrids commonly referred to as the Slash Pine. In alternative embodiments, the source material comprises a material derived from a member of the species *Pinus echinata* Mill, and its hybrids commonly referred to as Shortleaf Pine. In alternative embodiments, the source material comprises a material derived from a member of the species *Pinus palustris* Mill, and its hybrids commonly referred to as the Longleaf Pines. Southern Yellow Pines of the type disclosed herein are native to the Southeast United States and may typically be found along the coastal plain from eastern Texas to southeast Virginia extending into northern and central Florida. These Southern Yellow Pines are also globally cultivated and as such it is contemplated other regions may also provide a source of such pines. Typically Southern Yellow Pines are characterized as having a height of 30-35 m (100-115 ft) and a diameter of 0.7 m (28 in) and may grow to 47 m (154 ft) with a diameter of 1.2 m (47 in). Southern Yellow Pines may also be characterized by bark that is thick, reddish-brown, and scaly and leaves that are dark green, needle-like, and occur in bundles of up to three. The leaves are often twisted and have a length ranging from 20-45 cm (8-18 in).

In embodiments, a process of deriving a GROC from a source material (e.g., wood) comprises comminuting the source material, extracting soluble material from the source material, and concentrating the extracted solubles. In an embodiment, a process of deriving a GROC from a source material (e.g., wood) comprises comminuting the wood, extracting oligosaccharides and polysaccharides (e.g., hemicellulose) from the source material via contact with a solvent (e.g., water), and concentrating the solvent extract.

In an embodiment, the process of deriving a GROC from a source material optionally comprises comminution of the source material to reduce the physical size of the source material. For example, the wood source material may be chipped or comminuted prior to extracting the soluble material. As will be appreciated by those of skill in the art, comminuting the wood source material is an appropriate means of reducing the wood to a size that is both manageable and efficient for continued processing. Suitable machinery known to those of skill in the art may be employed to comminute the source material, non-limiting examples of which include tub grinders, wood chippers, chip-n-saws and the like. Further, the comminuted wood may be screened to ensure that the material is uniformly or substantially uniformly sized. In the following embodiments, it is presumed that the wood source material has been comminuted prior to further processing. Though one or more of the following embodiments may describe the performance of processes with respect to comminuted wood, it is specifically contemplated that comminution is not necessarily a prerequisite to these processes.

In an embodiment, the process of deriving a GROC from a source material (e.g., wood) comprises extracting the soluble material from the wood. Any method known to one of ordinary skill in the art and not deleterious to the GROC may be employed to extract the soluble material from the wood. In an embodiment, the process of extracting the soluble material from the wood comprises softening the source material (e.g., wood), optionally comminuting the softened wood, and contacting the softened wood with one or more solvents into which the soluble material may partition. Herein "softening" refers to processes which decrease the structural integrity of the exposed cell walls of the source material.

In an embodiment, the source material (e.g., wood) is softened using any methodology known to one of ordinary skill in the art and compatible with the components of the GROC. Nonlimiting examples of such methodologies include thermal, thermomechanical, thermochemical, mechanical, chemical, hydrothermal, acid hydrolysis, alkaline hydrolysis, organosolvent treatment, enzyme treatment, or combinations thereof. In an embodiment, the methodology comprises steam explosion and decompression wherein the source material is subjected to steam, pressure, and elevated temperature for some specified time period to soften and dissolve cell wall constituents.

In an embodiment, the source material is softened by a technique comprising autohydrolysis. As used herein, the term "autohydrolysis" refers to the process of subjecting the source material to a high temperature in the absence of chemicals but with moisture wherein organic acids are formed from functional groups such as acetyl groups liberated from the source material.

Specifically, the autohydrolysis process may comprise introducing the source material (e.g. comminuted wood) into a steam digester. In embodiments, the comminuted wood is steamed at a pressure ranging from 18-300 psi, alternatively, from 50-250 psi, alternatively, from 75-225 psi. In embodiments, the comminuted wood will be allowed to remain in the steam digester for a period up to 10 minutes, alternatively, up to 15 minutes, alternatively, up to 20 minutes. In an embodiment, temperatures within the steam digester range from 212-420° F., alternatively, from 290-340° F., alternatively, from 295-335° F., alternatively, from 300-330° F. Not seeking to be bound by any particular theory, introduction into the steam digester softens the woods chips, thereby increasing the efficiency of later processing steps which seek to extract the soluble material.

In an embodiment, the source material is softened by a technique comprising pulping. Any pulping process known to one of ordinary skill in the art and not deleterious to the GROC may be employed to soften the source material. Examples of such processes are described in greater detail below.

In an embodiment, the source material (e.g., comminuted wood) is pulped using a mechanical pulping process. In these embodiments, the mechanical pulping process comprises separating the component wood fibers via the use of a plurality of grindstones, refining discs, knives, and like machinery known to those of skill in the art to mechanically disintegrate the comminuted wood, thereby reducing the comminuted wood to the fibrous components.

In an embodiment, the source material is pulped by subjecting the material to a pulping agent. In these embodiments, the pulping process comprises subjecting the comminuted wood to one or more chemicals and/or enzymes which will break down the lignin that holds the fibrous components together. Thus, as the lignin is degraded, the fibers of the wood are separated. Nonlimiting examples of chemical pulping processes include acid hydrolysis, alkaline hydrolysis, organosolvent treatment and the like.

In some embodiments other methodologies for softening the source material may be employed. Such methodologies may employ a variety of reaction parameters such as temperature, pressure, pH, varying reaction times and the like to extract the soluble material from the wood. For example, the source material may be softened by a steam extrusion process. Herein steam extrusion refers to a process wherein the source material (e.g., comminuted wood) is pressed through a die where compressed gases (e.g., steam) are developed and then expanded (released).

Hereinafter the source material whether subjected to a process of the type described herein (e.g., optional comminution followed by autohydrolysis or pulping) is termed the refined source material and for simplicity will hereinafter be referred to as the "refined wood."

In some embodiments, the process further comprises comminuting the refined wood. Comminution and methods of carrying out same have been described previously herein and may likewise be used to reduce the size of the refined wood. The comminuted, refined wood may be passed for washing as described below.

The process of deriving a GROC from a source material may further comprise washing the refined wood. The refined wood may be washed by contacting the material with a wash solution. The wash solution may comprise any material compatible with the components of the GROC. In an embodiment, the wash solution is an aqueous solution; alternatively the wash solution is water or consists essentially of water. Contacting of the refined wood and wash solution may be carried out using any suitable technique such as for example by showering the refined wood with a wash solution. As the refined wood is contacted with the wash solution the extractable compounds may be dissolved in or otherwise portioned into the wash solution which may then be collected. In an embodiment, the soluble material comprising oligosaccharides and polysaccharides (e.g., hemicellulose) present in the refined wood will be dissolved, suspended in, or otherwise partitioned into the wash solution.

In some embodiments, softening of the source material and extraction of the soluble material may be carried out concomitantly using a process such as solid-liquid countercurrent extraction. Herein, solid-liquid countercurrent extraction refers to a process wherein a solid phase material (e.g., comminuted wood) and a liquid phase material (e.g., hot water) are contacted to each other by causing them to flow countercurrently to each other to adsorb part of the components contained in the liquid phase to the solid phase and simultaneously extract part of the components adsorbed to the solid phase into the liquid phase.

The wash solution obtained by the processes described herein comprises soluble material extractable from a source material of the type described previously herein. Hereinafter the wash solution obtained as described is termed the soluble extractable material ("SEM"). In an embodiment, processes of the type described herein result in the extraction of greater than about 50% of the hemicellulose present in the source material, alternatively greater than about 60, 65, 70, 75, or 80% of the hemicellulose present in the source material.

In an embodiment, the SEM may be further processed by concentrating the solution to form a concentrated liquid. In embodiments, the SEM is concentrated to between 40 and 70% solids, alternatively to between 12% to 40% solids, alternatively to between 70% to 90% solids. The solids found in the SEM comprise approximately 93% carbohydrate material, approximately 4% ash, and less than approximately 1% each of protein, fat, or crude fiber and exhibit methane-reducing activity.

In an embodiment, the SEM is dehydrated to remove excess moisture. The SEM may be dehydrated using any suitable dehydration process as known to those of skill in the art and compatible with the needs of the process (e.g., spray drying, drum drying). In an embodiment, the SEM may be dehydrated to a moisture content of less than about 18%, alternatively less than about 10%, alternatively less than about 5%. In an embodiment, the SEM is concentrated and/or dehydrated to yield a solids powder.

The SEM prepared as described herein may comprise monosaccharides, oligosaccharides and polysaccharides. The term oligosaccharide herein refers to a polymer comprising from about 2 to about 20 monosaccharide units while a polysaccharide herein refers to a polymer comprising greater than about 20 monosaccharide units. The number of monosaccharide units in a given oligosaccharide is termed the "degree of polymerization" (DP). For example, the SEM may comprise polysaccharides having a DP of greater than about 100, alternatively greater than about 150, 200, 250, 300, 350, 400, 450, or 500. In an embodiment, the SEM may comprise monomers, oligosaccharides, and polymers ranging from about 2 to about 500 DP as will be described in more detail later herein.

In embodiments the SEM comprises one or more oligosaccharides comprising a polysaccharide backbone; that is, the backbone comprises a plurality of glycosidically-linked monosaccharide units. In embodiments, the glycosidic linkage comprises an α-glycosidic link, a β-glycosidic link, or combinations thereof. In embodiments, the SEM comprises oligosaccharides comprising both α-glycosidic links and β-glycosidic links. In embodiments, the oligosaccharide will further comprise at least one side-chain. The side chain may comprise at least one monosaccharide unit glycosidically-linked to at least one saccharide unit of the polysaccharide backbone. Alternatively, the side chain may comprise at least one polysaccharide unit glycosidically-linked to at least one saccharide unit of the polysaccharide backbone.

In embodiments, the SEM comprises one or more oligosaccharides having monomeric units comprising an aldotriose monomer, an aldotetrose monomer, an aldopentose monomer, an aldohexose monomer, a ketotriose monomer, a ketotretrose monomer, a ketopentose monomer, a ketohexose monomer, a ribose monomer, an arabinose monomer, a xylose monomer, a lyxose monomer, an allose monomer, an altrose monomer, a glucose monomer, a mannose monomer, a gulose monomer, an idose monomer, a galactose monomer, a talose monomer, a ribulose monomer, a xylulose monomer, a psicose monomer, a fructose monomer, a sorbose monomer, a tagatose monomer, or combinations thereof.

In an embodiment, the SEM is further processed to reduce the DP of the constituent polymers. The DP of the SEM constituent polymers (e.g., polysaccharides) may be reduced by cleaving one or more of the glycosidic bonds between the monomer units of an oligosaccharide. Various methods can be used to cleave some of the glycosidic bonds between the monomer units while preserving the integrity of the sugar units. For example, the glycosidic bonds may be hydrolyzed. Hydrolysis of the glycosidic bonds can be achieved through any mechanism known to one of ordinary skill in the art and compatible with the needs of the process. For example hydrolysis of the glycosidic bonds may be carried out employing chemical, enzymatic, thermal, or ultrasonic processes. Process variables such as reagent concentration, pH, temperature, time, and reactant can determine the degree of hydrolysis. Thus, one of ordinary skill in the art with the benefits of this disclosure may select hydrolysis reaction conditions suitable for the production of specific polymer chain lengths.

In embodiments, the DP of the SEM constituent polymers is reduced by acid hydrolysis of the material. For example, an acid for cleaving glycosidic bonds suitably comprises a weak acid. Non-limiting examples of such a weak acid include trifluoroacetic acid (TFA), acetic acid, and oxalic acid. Alternatively, in embodiments, an acid for cleaving glycosidic bonds suitably comprises a strong mineral acid. Non-limiting examples of such a strong mineral acid include sulfuric acid and hydrochloric acid. In various embodiments, numerous combinations of exposure time, temperature, and acid concentration can be used to hydrolyze any large DP hemicellulose polysaccharides to the DP ranges disclosed herein.

In alternative embodiments, the DP of the SEM constituent polymers is reduced enzymatically. For example, enzymes may be employed to cleave the polymer chains at specific linkages. Numerous enzymes, including but not limited to β-mannanase and glucosidases, are suitable for use. Such enzymes and reaction conditions suitable for enzymatic cleavage of the SEM would be known to one of ordinary skill in the art with the aid and benefits of this disclosure.

Hydrolysis of the SEM as described herein produces a material hereinafter termed the "hydrolyzed hemicellulose material" ("HHM"). The HHM may have a DP of about 2 to about 30, alternatively about 2 to about 20, alternatively about 2 to about 15, alternatively about 2 to about 12. In an embodiment, the HHM comprises oligosaccharides having from about 3 to about 5 DP, alternatively from about 9 to about 14 DP, alternatively from about 16 to about 18 DP.

In an embodiment, the HHM or the SEM is further processed by contacting the material with a precipitating agent. Upon contact with a precipitating agent, HHM/SEM-derived oligosaccharide fractions having gas-reducing functionality of the type described herein may be precipitated from the solution. In embodiments, a material containing gas-reducing activity is precipitated from the HHM or SEM when the HHM or SEM is contacted with a precipitating agent comprising an alcohol. Alternatively, a material containing gas-reducing activity is precipitated from the HHM or SEM when the HHM or SEM is contacted with ethanol. Further processing of the mixture comprising the precipitant may include removing the precipitating agent (e.g., ethanol) using any suitable technique (e.g., evaporation). The resulting precipitated material, hereinafter termed the precipitated gas-reducing material ("PGM"), may be dried or re-suspended in an appropriate solvent.

Additional processing of the PGM may involve subjecting the material to enrichment methods in order to concentrate fractions having a specific DP or remove non-active (e.g., non-methane-reducing) compounds. In embodiments, the PGM is further enriched by subjecting the previously described SEM and/or its derivatives (e.g., HHM) to additional separation procedures. In these embodiments, such separation procedures include but are not limited to chromatographic separation, ion exchange separation, filtration, microfiltration, ultra filtration, or the like. Such a separation process may be employed to remove any remaining non-desirable materials (e.g., monosaccharide, lignin, salts, phenolics, ash, etc.) from the product composition. Additionally compounds, such as phenolics or lignin, may be removed at various points during processing.

In an embodiment, the SEM, HHM, and/or PGM comprise hemicellulose comprising xylans, arabinoxylans, galactoglucomannans, or combinations or derivatives thereof. In an embodiment, the SEM, HHM, and/or PGM comprise xylans. In some embodiments, the xylan is comprised of a backbone chain of xylose units which are linked by β-(1,4)-glycosideic bonds and branched by α-(1,2)-glycosidic bonds with 4-O-methylglucoronic acid groups. In some embodiments, O-acetyl groups replace the OH groups in the C2 and C3 groups. A partial structure of a xylan is shown in Structure 1:

Structure 1

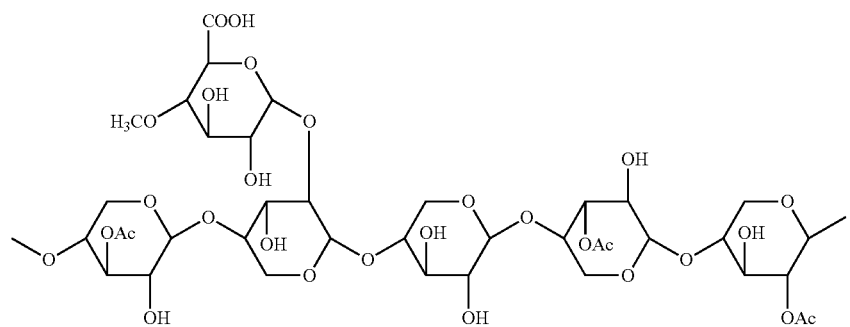

In an embodiment the SEM, HHM, and/or PGM comprise an arabinoxylan. Arabinoxylans consist of α-L-arabinofuranose residues attached as branch-points to β-(1→4)-linked D-xylopyranose polymeric backbone chains. These may be C2 or C3-substituted or C2 and C3-di-substituted. The arabinose residues may also be linked to other groups attached such as glucuronic acid residues, ferulic acid crosslinks and acetyl groups. The most stable conformations comprise α-L-arabinofuranose and β-(1→4)-linked D-xylopyranose residues. The furanose can, however, take up a number of other conformations with similar energy whereas the chair conformation of the pyranose residue is fixed. Arabinoxylans may comprise greater than about 500 monosaccharide repeating units, alternatively greater than about 1000 monosaccharide repeating units, alternatively from about 1500 to about 5000 monosaccharide repeating units. A partial structure of an arabinoxylan is shown in Structure 2:

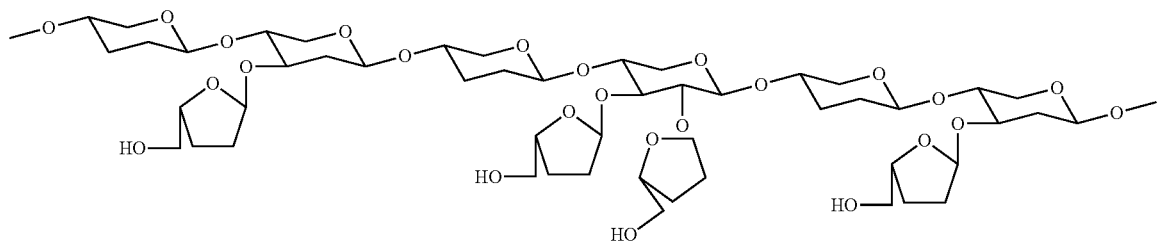

In embodiments, the SEM, HHM, and/or PGM comprise an oligosaccharide comprising monomeric units having glucose monomers, galactose monomers, and mannose monomers in the form of a galactoglucomannan ("GGM"). In embodiments, the GGM comprises a backbone of β-1-4 linked mannose units with randomly spaced glucose units included and occasional α-1-6 galactose unit side chains. In embodiments, the hydroxyl groups of one or more monomeric units comprising the GGM backbone are partially substituted with O-acetyl groups at C-2 and C-3 positions. A non-limiting representative GGM structure is shown in Structure 3:

Structure 3

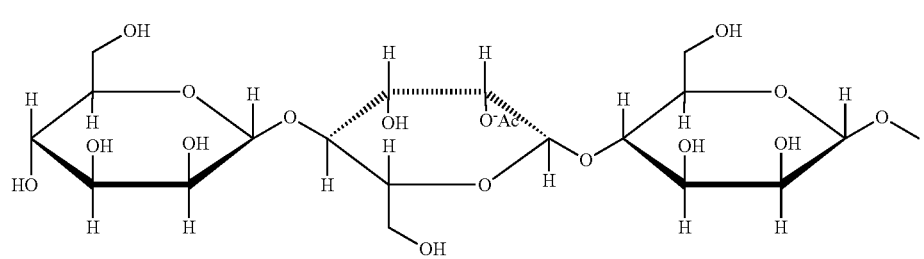

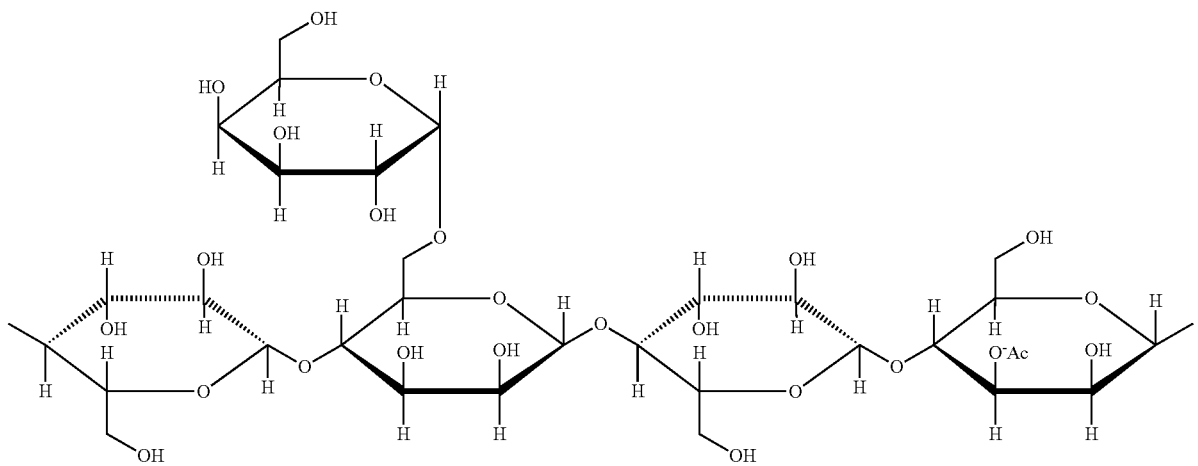

-continued

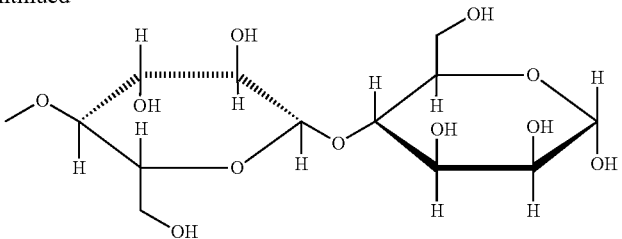

In an embodiment, the GGM oligosaccharide comprises glucose, galactose, and mannose in a ratio of 3 to 1 to 6 respectively.

As will be understood by one of ordinary skill in the art, variations in the methodology for obtaining the SEM, HHM, and/or PGM may result in variations in the amounts and/or nature of the components of the SEM, HHM, and/or PGM. Hereinafter the GROC which may comprise the SEM, HHM, and/or PGM may be administered to an organism in order to reduce gas production of the organism. In an embodiment, the organism has a gastrointenstinal tract. In some embodiments, the organism is a ruminant animal. Herein a ruminant animal refers a mammal of the order Artiodactyla that digests plant-based food by initially softening it within the animal's first stomach, known as the rumen, then regurgitating the semi-digested mass, now known as cud, and chewing it again.

In practical use, a GROC can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers may be employed. If desired, tablets may be coated by standard aqueous or nonaqueous techniques.

Pharmaceutical compositions comprising a GROC suitable for oral administration may be presented as discrete units such as capsules, cachets or tablets each containing a predetermined amount of the active ingredient (e.g., GROC), as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

The GROC may be used in combination with other compositions that are used in the treatment/prevention/suppression or amelioration of the adverse health events for which a GROC of the type described herein are useful.

In an embodiment, the GROC is administered to an organism of the type previously described herein. Administration of the GROC may comprise preparing the GROC in a suitable orally ingestible form and providing the suitable orally ingestible form to the organism. Suitable orally ingestible forms are discussed herein in further detail, although other suitable ingestible forms and methods of formulating same will be appreciable by those of skill in the art with the aid of this disclosure.

In an embodiment, a suitable orally ingestible form comprises a GROC incorporated within a food, feed, or fodder product. The GROC may be incorporated within the food, feed, or fodder product as a dry powder or a liquid. Non-limiting examples of food, feed, or fodder products into which the GROC may be incorporated include compound feeds and premixes such as pellets, liquid feed, nuts, nuggets, oil cakes, press cakes, various meals (e.g., fishmeal), or combinations thereof. Such food, feed, or fodder product may be prepared by admixing or blending the GROC with a suitable carrier or diluent. Non-limiting examples of suitable carriers may include grass and other forage plants, plant oils, seeds, grains, crop residues, sprouted grains, legumes, alfalfa meal, soybean meal, cottonseed oil meal, linseed oil meal, sodium chloride, cornmeal, molasses, urea, corncob meal, rice kernel, and the like. The carrier promotes a uniform distribution of the active ingredients in the finished feed into which the carrier is blended. It thus may ensure proper distribution of the active ingredient throughout the food, feed, or fodder product.

In an embodiment, a suitable orally ingestible form comprises a GROC prepared as a nutritional supplement. Such a nutritional supplement may be ingestible by an organism alone or with another food, feed, fodder, forage product, snack, treat, or enjoyment product. In various embodiments, nutritional supplements may be prepared in a wet, semi-wet, or dry form. Nonlimiting examples of suitable nutritional supplement forms include powders, granules, syrups, and pills; other suitable forms will be known to those of skill in the art with the aid of this disclosure. In an embodiment, a nutritional supplement may be added to another food, feed, fodder, or forage product. For example the nutritional supplement may comprise a powder or syrup which is dispensed with (e.g., poured onto) hay, pellets, forage, or the like. Alternatively, in an embodiment a nutritional supplement is provided without any other food or nutrient. For example, the nutritional supplement may comprise a syrup, gel, block, or tub which may be licked by an organism (e.g., from a tub or other suitable dispenser) or water-soluble powder dissolved in water provided for ingestion by the organism. Other suitable means of dispensing a nutritional supplement will be appreciated by those of skill in the art viewing this disclosure.

As will be appreciated by those of skill in the art, the ingestible forms may be formulated for ingestion by one or more organisms, non-limiting examples of which include livestock such as cattle, swine, horses, sheep, goats, poultry, fish, domesticated companionship species such as dogs, cats, fish, and rodents or undomesticated wildlife such as deer, moose, elk, migratory and non-migratory fowl, decapods, and fish.

In an embodiment, administration of a GROC improves the overall health of the organism to which it is administered. In some embodiments, the overall improved health of the organism may be evidenced by an increase in biological functions such as nutrient uptake, muscle growth, muscle development, weight gain, coat growth, survival, or combinations thereof. In another embodiment administration of the GROC to an organism results in an increased yield in an organism derived commodity such as eggs, meat, milk, wool, or combinations thereof.

In an embodiment, a ruminant animal when administered a GROC of the type described herein may display increased ruminal fermentation rates, increased dry matter digestion and a reduction in methane production when compared to an otherwise similar ruminant animal not administered a GROC. Without wishing to be limited by theory, administration of GROC of the type described herein to a ruminant animal may alter the pH of the ruminal environment resulting from an increased production of volatile fatty acids. In an embodiment, administration of GROC may selectively stimulate and/or inhibit the activity of certain microorganisms in the rumen. In an embodiment, administration of GROC of the type described herein to a ruminant animal results in a change in the production of specific volatile fatty acids, and in the relative proportion of specific volatile fatty acids. A decrease in the acetate:propionate ratio is consistent with reduced methane production. In an embodiment, administration of GROC of the type described herein to a ruminant animal results in a change in hexose and/or pentose fermentation in the ruminant animal.

EXAMPLES

Example 1

In this example, the effects of a GROC of the type described herein on microbial efficiency and metabolism were evaluated in continuous culture rumen fermentation. Rumen inoculum was fermented for ten days and samples were collected on days 8, 9, and 10. Three replications were conducted per treatment. Fermentation parameters were analyzed. The amount of propionic acid increased while the amount of acetic acid decreased with the inclusion of 1% GROC over the control. This was seen in the molar percentage as well and the mmoles per day measurements. See TABLE 1 for data. These fermentation parameters are consistent with the conditions favorable to the reduction of methane in the rumen.

TABLE 1

| Item | Control | With 1% GROC |
|---|---|---|
| Dry Matter Digestion (%) | 61.8 | 68.6 |
| Molar % Acetic Acid | 63.2 | 60.0 |
| Molar % Propionic Acid | 17.6 | 20.4 |
| Acetic:propionic ratio | 3.63 | 2.98 |
| Acetic acid (mmoles/day) | 251 | 240 |
| Propionic acid (mmoles/day) | 70 | 82 |

Example 2

Freshly collected ruminal contents containing mixed populations of ruminal bacteria were inoculated (1 g per tube) into 18×150 mm crimp top Hungate tubes filled with 9 ml anaerobic basal broth. The basal medium contained essential minerals, nutrients and vitamins was supplemented with finely ground alfalfa (2.0% wt/vol) and buffered to pH 6.80. GROC was included in sets of triplicate incubation doses at 0, 0.03, 0.10, 0.30 and 0.60 per 10 ml.

All incubations were conducted at 39° C. under a 100% $CO_2$ gas phase for 24 h. After 24 h incubation, gas volumes were measured by recording displacement of volume in a lubricated glass syringe and 1 ml headspace gas samples were injected into a gas chromatograph for determination of hydrogen, methane and carbon dioxide composition (Allison et al., 1992). Aliquots from each incubation tube were also measured for pH and for colorimetric determination of ammonia concentrations (Chaney and Marbach, 1962). Fluid samples collected at 0 and 24 h incubation were frozen and shipped to the National Animal Disease Center in Ames, Iowa for determination of volatile fatty acid accumulations by gas chromatography (Salanitro and Muirhead, 1975). A subsequent study was conducted similarly except using 0.02% (wt/vol) trypticase as an added protein substrate to assess the potential impact of GROC on protein and amino acid metabolism.

A general analysis of variance revealed main effects ($P<0.05$) of GROC on final pH and on total volume and composition of gas produced during in vitro incubation of mixed populations of ruminal microbes (FIGS. 1-5). Quadratic trends were observed for effects of GROC on accumulation of hydrogen and carbon dioxide with the highest amounts of these gases being produced in incubations supplemented with 0.10 g inclusion levels but with production declining rapidly in incubations supplemented with ≥0.3 g product. Linear effects of GROC were observed on pH and methane production. These results suggest that the lower inclusion levels of GROC had no direct negative effect on ruminal fermentation but at the higher inclusion levels an indirect effect of the lower pH likely inhibited gas production. This conclusion is supported by the observation of increasing amounts of formate, acetate, lactate and succinate produced in incubations supplemented with greater amounts of GROC. See TABLE 2. The production of these volatile fatty acids typically increases with readily fermentable substrates. The quadratic responses observed with respect to the production of the more reduced volatile fatty acids propionate, butyrate and valerate are not unexpected as these acids are inversely correlated with lactate production. Similarly, formate and succinate generally do not accumulate in ruminal fermentations unless methane production is decreased. A linear increase in amounts of hexose fermented was observed with increasing inclusion of GROC which indicates the product contained appreciable quantities of readily fermentable carbohydrate.

Figure 6:
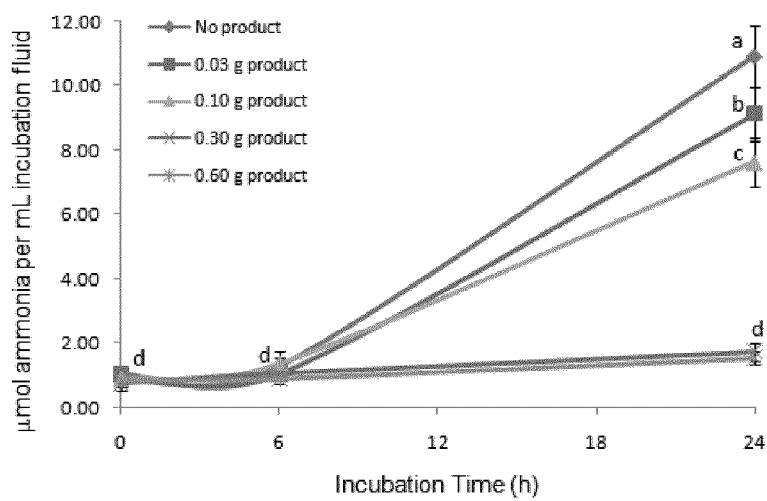
FIG. 6 represents the effect of GROC on ammonia accumulation during in vitro incubation of ruminal contents supplemented with 0.02 g ground alfalfa.

Using 0.02% tryptose, an enzymatic digest of soybean meal, to assess the potential impact of GROC on protein and amino acid metabolism has been analyzed. Results reveal that rates of ammonia accumulation (not shown) and the total amount of ammonia produced during incubation with added tryptose decreased with increasing GROC supplementation (FIG. 6). Rates of ammonia production by ruminal microbes are markedly influenced by pH with rates being highest near pH 8.0 and declining rapidly at pH<7.0. The pH measured at the end of the tryptose incubations declined linearly (P<0.05) with increasing GROC supplementation (6.61±0.02, 6.45±0.03, 5.98±0.05, 4.66±0.04 and 4.32±0.01 for incubations containing 0, 0.03, 0.10, 0.30 and 0.60 g added product, respectively) indicating that pH may have influenced protein catabolism in these incubations.

nant's rumen (or other subject animal's digestive system contents) may be multiplied by a representative GROC dosing factor of 0.003 g/ml, 0.01 g/ml, 0.03 g/ml, or 0.06 g/ml to correlate the dosage amounts of the GROC tested in vitro to in vivo amounts. That resulting value may then be divided by the mass of the subject to determine an amount of GROC per unit of body weight.

As will be understood by one of ordinary skill in the art, the amount of a composition (e.g., GROC) utilized to observe an in vitro response may differ significantly from that required to observe an in vivo response of the same type and magnitude. Particularly, the determination of in vivo dosing amounts and regimes is a multifactorial analysis that may be undertaken by the ordinarily skilled artisan using any suitable methodology. This disclosure contemplates determination of in vivo dosing

TABLE 2

Volatile fatty acid production and stoichiometric estimation of hexose fermentation during in vitro incubation of increasing concentrations of GROC with mixed populations of ruminal microbes in freshly collected rumen fluid supplemented with 0.2 g ground alfalfa.

| Volatile fatty acid production† | Treatment | | | | | SEM | P |
| --- | --- | --- | --- | --- | --- | --- | --- |
| | None | 0.03 | 0.10 | 0.30 | 0.60 | | |
| Formate ($\mu$mol ml$^{-1}$) | <0.15$^c$ | <0.15$^c$ | 1.45$^c$ | 10.77$^b$ | 19.10$^a$ | 0.58 | <0.0001 |
| Acetate ($\mu$mol ml$^{-1}$) | 42.57$^b$ | 40.79$^b$ | 53.53$^b$ | 56.87$^{ab}$ | 73.96$^a$ | 4.00 | 0.0011 |
| Propionate ($\mu$mol ml$^{-1}$) | 22.52$^c$ | 31.59$^b$ | 54.15$^a$ | 24.22$^c$ | 6.37$^d$ | 1.24 | <0.0001 |
| Butyrate ($\mu$mol ml$^{-1}$) | 3.74$^b$ | 3.83$^b$ | 9.88$^a$ | 1.47$^b$ | 0.31$^b$ | 0.84 | 0.0001 |
| Lactate ($\mu$mol ml$^{-1}$) | <0.15$^c$ | <0.15$^c$ | <0.15$^c$ | 76.32$^b$ | 109.31$^a$ | 0.20 | <0.0001 |
| Valerate ($\mu$mol ml$^{-1}$) | 0.51$^b$ | 0.24$^b$ | 3.01$^a$ | 0.17$^b$ | <0.15$^b$ | 0.14 | <0.0001 |
| Isobutyrate ($\mu$mol ml$^{-1}$) | 0.21$^a$ | 0.15$^b$ | <0.15$^b$ | <0.15$^b$ | <0.15$^b$ | 0.37 | 0.0050 |
| Isovalerate ($\mu$mol ml$^{-1}$) | <0.15$^b$ | <0.15$^b$ | <0.15$^b$ | <0.15$^b$ | 0.21$^a$ | 0.02 | <0.0002 |
| Succinate ($\mu$mol ml$^{-1}$) | 0.96$^c$ | 0.64$^c$ | 3.14$^{bc}$ | 9.91$^a$ | 4.74$^b$ | 0.63 | <0.0001 |
| Total ($\mu$mol ml$^{-1}$) | 70.67$^d$ | 77.33$^d$ | 125.42$^c$ | 180.40$^b$ | 215.01$^a$ | 5.95 | <0.0001 |
| Acetate:Propionate ratio | 1.89$^{bc}$ | 1.29$^{bc}$ | 0.99$^c$ | 2.35$^b$ | 11.60$^a$ | 0.25 | <0.0001 |
| Stoichiometric calculations‡ | | | | | | | |
| Hexose fermented ($\mu$mol ml$^{-1}$) | 15.91$^d$ | 26.07$^c$ | 49.53$^{ab}$ | 43.89$^b$ | 53.63$^a$ | 1.81 | <0.0001 |

†Tests for effect of GROC level were conducted via a general analysis of variance. Values are the mean from cultures incubations in triplicate.
‡Amounts of hexose fermented were calculated as ½ acetate + ½ propionate + butyrate + valerate (DeMeyer, 1991).
$^{a,b,c,d}$Means within rows with unlike superscripts differ (P < 0.05) based on a Tukeys All-Pairwise Comparison test.

As can be seen from Example 2, the amount of methane produced significantly decreased as the amount of composition increased.

To determine a gas reducing composition dosing regime, a dosing factor may be utilized. Dosing factors may be calculated utilizing accepted/customary methodologies and/or procedures to derive the desired and/or effective amount of GROC to be provided to a subject animal.

The dosing factor may be in the range of about 0.0001 g/ml to 0.1000 g/ml. In embodiments the dosing factor may be about 0.0001 g/ml, 0.0002 g/ml, 0.0005 g/ml, 0.0010 g/ml, 0.0015 g/ml, 0.0020 g/ml, 0.0025 g/ml, 0.0030 g/ml, 0.0035 g/ml, 0.0040 g/ml, 0.0045 g/ml, 0.0050 g/ml, 0.0055 g/ml, 0.0060 g/ml, 0.0065 g/ml, 0.0070 g/ml, 0.0075 g/ml, 0.0080 g/ml, 0.0085 g/ml, 0.0090 g/ml, or 0.0095 g/ml. In other embodiments, the dosing factor may be about 0.0100 g/ml, 0.0150 g/ml, 0.0200 g/ml, 0.0250 g/ml, 0.0300 g/ml, 0.0350 g/ml, 0.0400 g/ml, 0.0450 g/ml, 0.0500 g/ml, 0.0550 g/ml, 0.0600 g/ml, 0.0650 g/ml, 0.0700 g/ml, 0.0750 g/ml, 0.0800 g/ml, 0.0850 g/ml, 0.0900 g/ml, 0.0950 g/ml, or 0.1000 g/ml. In all of the above-stated embodiments, the variance in the stated values may range from about 1% to 50%.

In an embodiment, test doses of 0.03 g, 0.10 g, 0.30 g, and 0.60 g of GROC per 10 ml incubation fluid correspond to GROC dosing factors of 0.003 g/ml, 0.01 g/ml, 0.03 g/ml, and 0.06 g/ml, respectively. As such, to determine the appropriate dosing regime, the volume of the embodiment's subject rumiamounts and regimens effective to produce the beneficial properties disclosed herein (e.g., reduction in methane production by an organism). Further this disclosure contemplates the in vivo dosing amounts effective to produce the beneficial properties disclosed herein may differ significantly from the in vitro dosing amounts disclosed to produce beneficial properties of the same type and magnitude.

For example, assuming a mature ruminant has a mass of approximately 500 kg and has a rumen volume of 60 liters (60,000 ml), the in vitro test concentrations are multiplied by a 60,000 ml rumen volume to yield 180 g, 600 g, 1800 g, and 3600 g per ruminant, respectively. Thus, for a ruminant having a mass of 500 kg, the corresponding doses would be administered as 0.36 g/kg, 1.2 g/kg, 3.6 g/kg, and 7.2 g/kg, respectively, to correlate the dosage concentrations of the GROC tested in vitro to in vivo amounts.

Alternatively, the percentage of dry matter consumed relative to body mass may be utilized to calculate the amount of GROC to be added to an amount of dry matter to achieve the desired GHG production reduction. In an embodiment, a ruminant may consume 2.5% of its body mass per day in dry matter (e.g., feed or other dietary intake). Thus, to determine the appropriate GROC dosing regime, the subject animal's mass and rumen volume may be used in conjunction with the subject animal's daily dry matter intake to calculate the amount of GROC to be added to an amount of dry matter to achieve the desired GHG production reduction.

For example, considering a hypothetical ruminant having a mass of 500 kg and a rumen volume of 60 liters, representative GROC dosing factors of 0.003 g/ml, 0.01 g/ml, 0.03 g/ml, or 0.06 g/ml would correspond to in vivo GROC amounts of 180 g, 600 g, 1800 g, and 3600 g, respectively. As such, again considering that a ruminant consumes 2.5% of its body mass per day in dry matter, the corresponding amount consumed for the 500 kg ruminant would be 12,500 g of dry matter. Thus, calculating the percentage of GROC included in the ruminant's diet corresponding to the dosage concentrations of the GROC tested in vitro, the corresponding calculated in vivo amounts of GROC (e.g., 180 g, 600 g, 1800 g, and 3600 g) should be divided by the calculated amount of dry matter (e.g., 12,500 g) to derive the appropriate percentage of GROC to be supplemented by mass to the ruminant's diet.

Accordingly, the percent supplementation of GROC for the above hypothetical ruminant would be: 180 g GROC/12500 dry matter=1.4% GROC supplementation; 600 g GROC/12500 g dry matter=4.8% GROC supplementation; 1800 g GROC/12500 g dry matter=14.4% GROC supplementation; and 3600 g product/12500 g dry matter=28.8% GROC supplementation. These percentages, 1.4%, 4.8%, 14.4%, and 28.8% for in vivo dry matter supplementation correspond to the achieved percentage gas production effects indicated in FIGS. 1-4 for the in vitro test amounts of GROC 0.03 g, 0.10 g, 0.30 g, and 0.60 g, respectively.

Specifically, for an embodiment, a 14.4% supplementation of GROC in a ruminant's dry matter diet would result in about a 12% decrease in the amount of total ruminal gas produced by said ruminant. A 28.8% supplementation of GROC in a ruminant's dry matter diet would result in about a 35% decrease in the amount of total ruminal gas produced by said ruminant. These reductions are surprising and unexpected because both a 1.4% and 4.8% supplementation of GROC in a ruminant's dry matter diet result in increases in total ruminal gas production.

Specifically, for an embodiment, a 1.4% supplementation of GROC in a ruminant's dry matter diet would result in about a 30% decrease in the amount of ruminal methane produced by said ruminant. A 4.8% supplementation of GROC in a ruminant's dry matter diet would result in about a 50% decrease in the amount of ruminal methane produced by said ruminant. A 14.4% supplementation of GROC in a ruminant's dry matter diet would result in a 95% decrease in the amount of ruminal methane produced by said ruminant. A 28.8% supplementation of GROC in a ruminant's dry matter diet would result in a 99% decrease in the amount of ruminal methane produced by said ruminant. These reductions are surprising and unexpected because both a 1.4% and 4.8% supplementation of GROC in a ruminant's dry matter diet result in increases in total ruminal gas production as well as carbon dioxide production while resulting in simultaneous decreases in ruminal methane production.

Specifically, for an embodiment, a 14.4% supplementation of GROC in a ruminant's dry matter diet would result in about a 12% decrease in the amount of ruminal carbon dioxide produced by said ruminant. A 28.8% supplementation of GROC in a ruminant's dry matter diet would result in about a 66% decrease in the amount of ruminal carbon dioxide produced by said ruminant. These reductions are surprising and unexpected because both a 1.4% and 4.8% supplementation of GROC in a ruminant's dry matter diet result in increases in ruminal carbon dioxide production.

A supplementation/dosing regime could comprise supplementing a ruminant's dry matter diet with up to about 50% of GROC to result in each of a total ruminal gas production reduction, a ruminal methane production reduction, and a ruminal carbon dioxide production reduction.

A supplementation/dosing regime could comprise supplementing a ruminant's dry matter diet with approximately 10% to 30% of GROC to result in each of a total ruminal gas production reduction, a ruminal methane production reduction, and a ruminal carbon dioxide production reduction.

Example 3

In this example, the effects of a GROC of the type described herein on fiber degradation rates were evaluated in 12 multiparous Holstein cows (142±44 days in milk, 685±19 kg body weight) including four with ruminal fistula were used in a 2×2 Latin square with 21-d periods. Two diets were fed—(i) a control typical Midwest diet containing 55:45 forage (⅔ corn silage, ⅓ alfalfa hay) to concentrate ratio; and (ii) a treatment diet in which 1.0% of the diet dry matter ("DM") was replaced with GROC. DM intake averaged 27.1 and 26.9 kg/d for the control and treatment, respectively, and was not affected by treatment.

In situ testing was performed using Dacron bags containing corn silage, alfalfa hay, or control or treatment total mixed ration ("TMR"). The bags were inserted in triplicate into the rumens of the 4 fistulated cows, TMR corresponding to the current diet. The bags were incubated for from 0 to 48 hours, and degradation of forages and TMR were analyzed. The in situ fiber disappearance data is shown in TABLE 3. The increase in fiber degradation rates of forages and diets with the inclusion of GROC demonstrates the ability of the material in affect ruminal digestion and/or fermentation.

For corn silage, the rate of disappearance (Kd) of neutral detergent fiber ("NDF") (1.7 vs. 4.3) and acid detergent fiber ("ADF") (1.8 vs. 4.7%/h) increased ($P<0.05$) for cows fed the treatment diet.

For alfalfa hay, the disappearance of fraction A of DM, NDF, and ADF decreased and fraction B of DM and NDF increased with treatment ($P<0.05$). The Kd for DM (8.0 vs. 11.0), NDF (6.3 vs. 10.3), and ADF (5.5 vs. 9.2) increased greatly for the alfalfa hay in rumens of treated cows ($P<0.05$).

The results of EXAMPLE 3 demonstrate that supplementing diets of lactating dairy cows with GROC has a beneficial effect on fiber degradation characteristics.

TABLE 3

|  | Control | Treatment | p < |
|---|---|---|---|
| In Situ DM Disappearance | | | |
| Alfalfa Hay | | | |
| A | 32.4 | 26.7 | 0.04 |
| B | 35.2 | 41.6 | 0.06 |
| Kd | 8 | 11 | 0.05 |
| In Situ NDF Disappearance | | | |
| Alfalfa Hay | | | |
| A | 9.4 | 3.6 | 0.02 |
| B | 33.1 | 38.9 | 0.06 |
| Kd | 6.3 | 10.3 | 0.01 |
| Corn Silage | | | |
| Kd | 1.7 | 4.27 | 0.05 |
| TMR | | | |
| A | 9.6 | 20.2 | 0.01 |

TABLE 3-continued

|  | Control | Treatment | p < |
|---|---|---|---|
| In Situ ADF Disappearance | | | |
| Alfalfa Hay | | | |
| Kd | 5.5 | 9.2 | 0.01 |
| Corn Silage | | | |
| Kd | 1.8 | 4.7 | 0.01 |
| TMR | | | |
| A | 11.4 | 17.1 | 0.03 |

An animal, when administered GROC, may display a reduction in GHG production, e.g., a reduction in methane production and/or carbon dioxide production, as compared to an otherwise similar or same animal not administered GROC. The GHG reduction may be associated with digestive activities of the animal, e.g., cud formation, sustenance breakdown, manure deposition, or combinations thereof.

Figure 3:
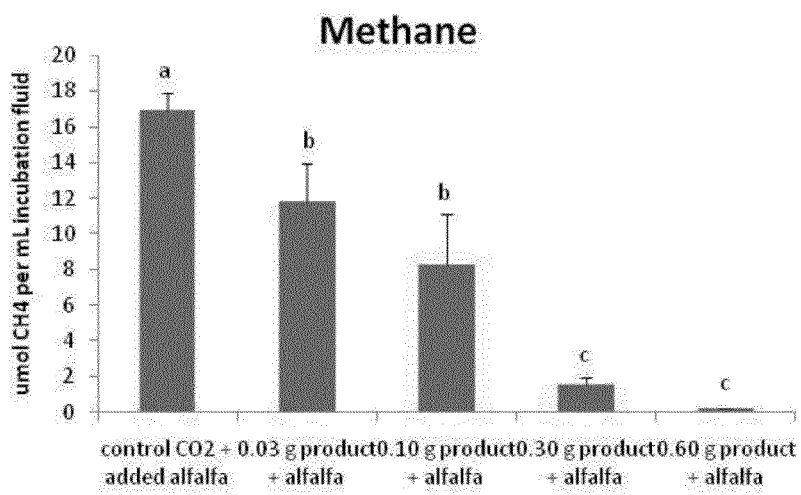
FIG. 3 represents the effect of GROC on methane production during in vitro incubation of ruminal contents supplemented with 0.02 g ground alfalfa.
Figure 4:
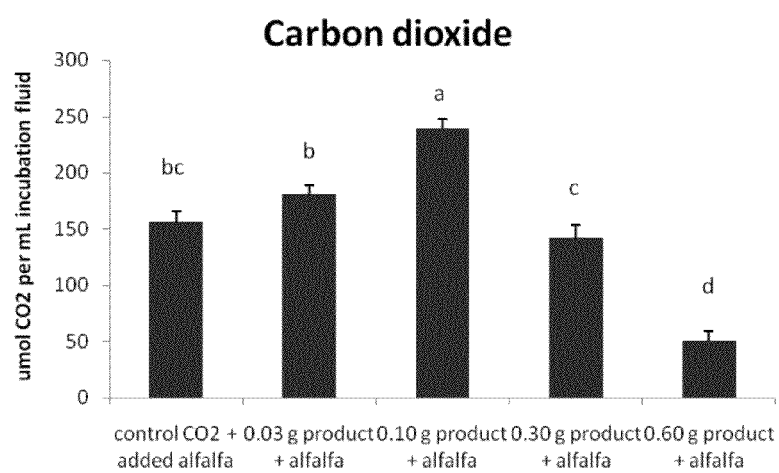
FIG. 4 represents the effect of GROC on carbon dioxide production during in vitro incubation of ruminal contents supplemented with 0.02 g ground alfalfa.
Figure 5:
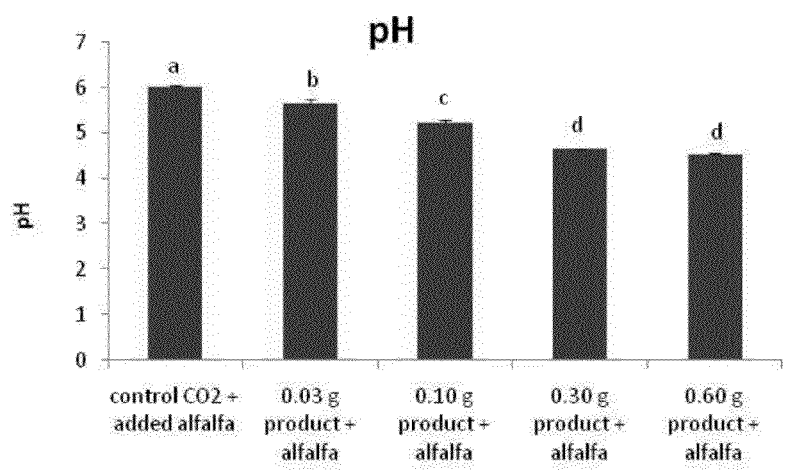
FIG. 5 represents the effect of GROC on final pH during in vitro incubation of ruminal contents supplemented with 0.02 g ground alfalfa.

As is evident in FIGS. 3 and 4, significant reductions in the amounts of methane and carbon dioxide can be achieved via the administration of GROC.

As shown in FIG. 3, the amount of ruminal methane produced can be significantly reduced via the introduction of GROC into a ruminant's diet. For example, FIG. 3 indicates that, depending on the proportion of GROC administered in relation to the remainder of the ruminant's diet, ruminal methane production can be decreased. The decrease in ruminal methane production can be in the range from about 1% to about 99%. For example, the decrease in ruminal methane production can be from about 5%, 10%, 15%, 20%, 25%, 30%, 35%, 40%, 45%, 50%, 55%, 60%, 65%, 70%, 75%, 80%, 85%, 90%, 95%, up to about 99%. Preferably, the decrease in ruminal methane production can be in the range from about 30% to about 99%.

As shown in FIG. 4, the amount of ruminal carbon dioxide produced can be significantly reduced via the introduction of GROC into a ruminant's diet. For example, FIG. 4 indicates that, depending on the proportion of GROC administered in relation to the remainder of the ruminant's diet, ruminal carbon dioxide production can be decreased. The decrease in ruminal carbon dioxide production can be in the range from about 1% to about 99%. For example, the decrease in ruminal carbon dioxide production can be from about 5%, 10%, 15%, 20%, 25%, 30%, 35%, 40%, 45%, 50%, 55%, 60%, 65%, 70%, 75%, 80%, 85%, 90%, 95%, up to about 99%. Preferably, the decrease in ruminal carbon dioxide production can be in the range from about 10% to about 66%.

The above reductions in carbon dioxide and methane may be utilized by farmers and producers as resulting carbon credits. Carbon credit as used herein is a generic term meaning that a value has been assigned to a reduction or offset of GHG emissions for sale, trading, or regulatory permitting and/or compliance purposes.

Every GHG has a global warming potential ("GWP"), a measurement of the impact that particular gas has on "radiative forcing"; that is, the additional heat/energy which is retained in the Earth's ecosystem through the addition of this gas to the atmosphere.

The GWP of a given gas describes its effect on climate change relative to a similar amount of carbon dioxide. As the base unit, carbon dioxide's GWP numeric is 1.0. This allows regulated GHGs to be converted to the common unit of carbon dioxide equivalents ("$CO_2e$"). For example, methane, a $CO_2e$, has a GWP of 21—meaning that one ton of methane will have an effect on global warming that is 21 times greater than one ton of carbon dioxide.

Carbon trading is an application of an emissions trading approach. GHG emissions are capped and then markets are used to allocate the emissions among the group of regulated sources. The goal is to allow market mechanisms to drive industrial and commercial processes in the direction of low emissions or less carbon intensive approaches than those used when there is no cost to emitting carbon dioxide and other GHGs into the atmosphere. Since GHG reduction projects generate credits, this approach can be used to finance carbon reduction schemes between trading partners and around the world.

Climate exchanges have been established to provide a spot market in allowances, as well as futures and options market to help discover a market price and maintain liquidity. Currently there are five exchanges trading in carbon allowances: the Chicago Climate Exchange, European Climate Exchange, Nord Pool, PowerNext and the European Energy Exchange.

Carbon prices are normally quoted in Euros per ton of carbon dioxide or its carbon dioxide equivalent ($CO_2e$). Other GHGs, e.g., methane, can also be traded, but as indicated, are quoted as standard multiples of carbon dioxide with respect to their GWP. These features reduce a GHG's cap's financial impact on business, while ensuring that the GHG's limits are met at a national and international level.

Farmers and producers who supplement their livestocks' diets with GROC may benefit from both international and national emissions trading mechanisms by converting and/or applying their livestocks' reductions in GHG, e.g., carbon dioxide and methane, to carbon credits and then monetizing those carbon credits on the appropriate climate exchanges.

For example, the United States Environmental Protection Agency reports that globally, ruminant livestock produce about 80 million metric tons of methane annually, accounting for about 28% of global methane emissions from human-related activities. In the U.S., cattle emit about 5.5 million metric tons of methane per year into the atmosphere, accounting for 20% of U.S. methane emissions.

A single adult cow, by itself, may emit 80-110 kg of methane per year. This means a farmer or producer with only 10 head of cattle could be responsible for 1 metric ton of methane per year. Accordingly, a farmer or producer with 100,000 head of cattle could be responsible for 10,000 metric tons of methane per year. Thus, if that farmer or producer were to utilize GROC in their livestock's diet, that farmer or producer could reduce their livestock's methane production by 5%, 10%, 15%, 20%, 25%, 30%, 35%, 40%, 45%, 50%, 55%, 60%, 65%, 70%, 75%, 80%, 85%, 90%, 95%, up to about 99%—i.e, tons of GHGs could be effectively prevented from entering the environment/atmosphere.

Similarly, if that farmer or producer were to utilize GROC in their livestock's diet, that farmer or producer could also reduce their livestock's ruminal carbon dioxide production by 5%, 10%, 15%, 20%, 25%, 30%, 35%, 40%, 45%, 50%, 55%, 60%, 65%, 70%, 75%, 80%, 85%, 90%, 95%, up to about 99%—again, effectively preventing tons of GHGs from entering the environment/atmosphere.

Converting such percentage reductions into methane and/or carbon dioxide tonnage reductions would allow said farmer or producer to convert such reductions into carbon credits. In order to convert the GHG production reductions into carbon credits, the farmer or producer must first establish a baseline value for their GHG producing activities. This baseline value would be determined: (i) based on the amount of GHG emissions expected pursuant to established emissions values and/or metrics for similarly situated activities sans any GHG emissions reducing endeavors; (ii) based on actually measured GHG emissions via accepted and/or established GHG emission measuring protocols and procedures (prior to GHG reducing endeavors); or (iii) by way of any other acceptable baseline establishing method and/or procedure. GHG emission reductions could then be quantified: (i) by projecting and/or extrapolating measured and/or calculated in vitro or simulated GHG emission reducing effects as in vivo/onsite reductions of GHG emissions; (ii) by actually measuring GHG emissions via accepted and/or established GHG emission measuring protocols and procedures; or (iii) by way of any other acceptable quantification method and/or procedure.

A GHG emitting entity/facility may be subject to certain designated/allowed levels of emissions for various types of GHG as established or promulgated by an authorized emissions governing/enforcing entity. As such, should said GHG emitting entity/facility emit GHG at levels below the designated/allowed levels, said GHG emitting entity/facility could convert its designated/allowed yet non-emitted amounts of GHG to carbon credits. For conversion purposes, one carbon credit is typically considered equivalent to one metric ton of $CO_2$ (or $CO_2e$) emissions.

The resulting carbon credits could then be traded on various climate exchanges to effectively monetize the GROC's effect on livestock for the economic/revenue benefit of the farmer or producer.

Such monetization, coupled with GROC's ability to reduce livestock-derived GHG while maintaining the livestock's feed intake and protein synthesis, e.g., providing for optimal livestock health, meat, and dairy production—unlike other similarly directed plant-based feed additives, would allow farmers and producers to maximize the economic output of their livestock management operations.

For example, as a result of supplementing their livestock's diets with GROC, farmers and producers would be able to optimize the health, size, and output of their livestock (to maximize the economic returns on such livestock's typical commodity-type concerns) while also converting the GROC-derived reductions in GHGs into carbon credits (to create and maximize an alternative livestock economic/revenue concern).

Such methods and systems of realizing the synergistic effects of GROC-supplemented livestock management benefits farmers and producers, consumers of said livestock's products, and all other persons concerned with reducing GHG emissions and protecting the environment/atmosphere.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$, and an upper limit, $R_U$, is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The discussion of any reference herein is not an admission that it is prior art to the presently disclosed subject matter, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A method of managing a livestock comprising:
    supplementing the livestock's diet with up to 50% by weight of the livestock's consumed dry matter per day a gas reducing composition comprising a soluble extractable material extracted from a lignocellulosic source;
    quantifying an amount of a reduction in a gas produced by the livestock subsequent to the supplementation, wherein the amount of the reduction in a methane gas is more than 50%, the amount of the reduction in a carbon dioxide gas is more than 12%, or combinations thereof;
    receiving at least one carbon credit from the methane reduction, carbon dioxide reduction, or combinations thereof; and
    receiving an economic benefit from monetizing the at least one carbon credit.

2. The method of claim 1, wherein the supplementing the livestock's diet with the gas reducing composition is based upon calculating an amount of the gas reducing composition necessary to effectuate a desired reduction in gas produced by the livestock.

3. The method of claim 2, wherein the calculating comprises:
    determining the livestock's ruminal volume;
    determining a gas reducing composition dosing factor;
        multiplying the ruminal volume and the gas reducing composition dosing factor.

4. The method of claim 2, wherein the calculating comprises:
    determining the livestock's mass;
    determining the livestock's ruminal volume;
    determining the livestock's percentage of body mass consumed in dry matter per day;
    determining a gas reducing composition dosing factor;
    multiplying the livestock's ruminal volume by the gas reducing composition dosing factor;
    multiplying the livestock's mass by the livestock's percentage of body mass consumed in dry matter per day;
    dividing the product of the livestock's ruminal volume and the gas reducing composition dosing factor by the product of the livestock's mass and the livestock's percentage of body mass consumed in dry matter per day, wherein a quotient of the product of the livestock's ruminal volume and the gas reducing composition dosing factor divided by the product of the livestock's mass and the livestock's percentage of body mass consumed in dry matter per day represents a percent of a livestock's dry matter diet comprising the gas reducing composition.

5. The method of claim 3, wherein the gas reducing composition dosing factor is in a range of 0.0001 g/ml to 0.1000 g/ml.

6. The method of claim 5, wherein the gas reducing composition dosing factor is in the range of 0.003 g/ml to 0.06 g/ml.

7. The method of claim 1, wherein the amount of the gas reducing composition is in a range of about 10% to about 30% by weight of the livestock's consumed dry matter per day.

8. A method of managing a livestock, comprising:
determining a baseline amount of greenhouse gases produced by the livestock;
administering to the livestock up to 50% by weight of the livestock's consumed dry matter per day a gas reducing composition comprising a soluble extractable material extracted from a lignocellulosic source;
determining an amount of an reduction in greenhouse gases produced by the livestock subsequent to the administering the gas reducing composition, wherein the amount of the reduction in a methane gas is more than 50%, the amount of the reduction in a carbon dioxide gas is more than 12%, or combinations thereof;
receiving at least one carbon credit from the methane reduction, carbon dioxide reduction, or combinations thereof; and
receiving an economic benefit from monetizing the at least one carbon credit.

9. The method of claim 1, wherein the economic benefit comprises a value assigned to the reduction in gas for sale, trading, regulatory permitting, compliance purposes, or combinations thereof.

10. The method of claim 1, wherein the carbon credit is traded on a public exchange.

11. The method of claim 1, wherein the carbon credit is used as an offset for an industrial gas-producing process.

12. The method of claim 1, wherein the gas is associated with digestive activities of the livestock.

13. The method of claim 12, wherein the digestive activities comprise cud formation, sustenance breakdown, manure deposition, or combinations thereof.

14. The method of claim 4, wherein the gas reducing composition dosing factor is in a range of 0.0001 g/ml to 0.1000 g/ml.

15. The method of claim 14, wherein the gas reducing composition dosing factor is in the range of 0.003 g/ml to 0.06 g/ml.

16. The method of claim 8, wherein the economic benefit comprises a value assigned to the reduction in gas for sale, trading, regulatory permitting, compliance purposes, or combinations thereof.

17. The method of claim 8, wherein the carbon credit is traded on a public exchange.

18. The method of claim 8, wherein the carbon credit is used as an offset for an industrial gas-producing process.

* * * * *